United States Patent [19]

Meer et al.

[11] Patent Number: 5,073,370
[45] Date of Patent: * Dec. 17, 1991

[54] LOW CALORIE, HIGH FIBER LAXATIVE

[75] Inventors: E. Harvey Meer, Cresskill; Frank Mountain, Ridgewood; Herbert V. Schultz, Jersey City, all of N.J.

[73] Assignee: Meer Corporation, North Bergen, N.J.

[*] Notice: The portion of the term of this patent subsequent to Feb. 26, 2008 has been disclaimed.

[21] Appl. No.: 660,406

[22] Filed: Feb. 22, 1991

Related U.S. Application Data

[63] Continuation of Ser. No. 275,714, Nov. 23, 1988, Pat. No. 4,996,051.

[51] Int. Cl.$^5$ ............................................. A61K 35/78
[52] U.S. Cl. .................................. 424/195.1; 514/892; 426/615
[58] Field of Search ...................... 424/195.1; 514/892; 426/615

[56] References Cited

U.S. PATENT DOCUMENTS 4,996,051  4/1991  Meer et al. ........................ 424/195.1

Primary Examiner—John W. Rollins
Attorney, Agent, or Firm—McAulay Fisher Nissen Goldberg & Kiel

[57] ABSTRACT

A natural fiber laxative is provided which consists of psyllium husk, apple fiber, fructose, gum arabic and flavorants. The psyllium husk and the apple fiber constitute together at least 75% by weight of the composition. The granular components are controlled to have a particle size less than that determined by a No. 50 mesh, thereby improving mouthfeel. The composition is, in addition to being all natural, low in calorie and high in fiber and when mixed with water has a palatable mouthfeel.

4 Claims, No Drawings

LOW CALORIE, HIGH FIBER LAXATIVE

This is a continuation of application Ser. No. 275,714 filed Nov. 23, 1988, now U.S. Pat. No. 4,996,051.

BACKGROUND OF THE INVENTION

The present invention relates to a low calorie, high fiber laxative and more specifically to such a laxative which is mixable with water for use as a laxative and which may be used in conjunction with a medically supervised dietary program to impart a feeling of satiety.

Dietary fiber is that portion of plant substances which are resistant to digestion. There is both soluble and insoluble fiber. Insoluble fiber passes through the digestive system substantially intact. It passes through more quickly than does soluble fiber and as such helps prevent constipation and also helps in treatment of diverticulosis and irritable bowel syndrome. It has recently been suggested that insoluble fiber may lessen the risk of colon cancer by passing carcinogens through the system more quickly.

Soluble fiber absorbs water. It does not dissolve in water but rather acts like a sponge in the small intestine and stomach, giving a feeling of satiety and permitting slow food absorption so as to make it useful in weight control and the treatment of diabetes. Soluble fiber is found in fruits and vegetables, especially in citrus fruits and apples.

Among the known sources of fiber usable as a laxative is psyllium powder. Various commercial products, containing psyllium powder are presently sold. Examples of such products are Fiberall, made by Rydelle Laboratories, Inc. of Racine, Wis., a bulk forming laxative which contains refined hydrophilic mucilloid extracted from the husk of psyllium seed, and Metamucil made by Proctor and Gamble of Cincinnatti, Ohio, a bulk laxative containing hydrophilic mucilloid derived from the husk of psyllium seed. Fiberall and Metamucil are both available in flavored and in unflavored forms. These products contain artificial ingredients and/or are high in calorie.

U.S. Pat. No. 4,698,232 discloses a fiber-containing nougat type candy. The main source of fiber in the candy is cereal bran, however, alternative sources of fiber disclosed in the patent are psyllium powder and apple fiber. The '232 Patent also contains among other ingredients gum arabic and a non-sucrose sweetener.

Dry fiber products which incorporate psyllium powder are disclosed in U.S. Pat. Nos. 4,551,331; 4,565,702; 4,609,831; and 4,668,519.

For people who need to improve bowel regularity and who are health and diet conscious, it is preferable to use a high fiber laxative which is made with all natural constituents and which is low in calories. Additionally, such a product should have both an appealing flavor and consistency. The cost of the product is also important since dry fiber bulking agents, unlike other laxative formulations, are intended for long-term daily use. By itself psyllium powder although a good source of fiber is expensive. Further, psyllium powder has a gritty, granular consistency when mixed with water and this consistency is not made more palatable by the use of flavoring.

It is an object of the present invention to provide a laxative bulking agent which is relatively low in cost, high in soluble fiber, low in calories, appealing in flavor and mouthfeel and all natural.

BRIEF DESCRIPTION

In one embodiment of the present invention, a dry high fiber laxative is provided which incorporates psyllium powder, apple fiber, apple flavoring, fructose and gum arabic. The psyllium powder and the apple fiber together constitute about 75% by weight of the composition. The psyllium powder, apple fiber and fructose all have a small particle size, no greater than approximately a 50 mesh size in that embodiment. The laxative is low in calories, high in dietary fiber, all natural, and relatively low in cost. Additionally, it has an acceptable flavor and consistency.

DETAILED DESCRIPTION OF THE PREFERRED EMBODIMENT

The laxative of the present invention is comprised of psyllium husks, apple fiber, fructose, spray dried apple flavor, and spray dried gum arabic.

Psyllium husk is the clean, dried seed coat obtained from the seeds of certain plants including *Plantago ovata* Forskal. Psyllium husk is commercially available in two purity levels—85% and 95% pure husk. The impurity is substantially endosperm from the seed. Psyllium seed husk is a natural polysaccharide composed of about 98% mucilage. In certain preparations it acts as expanded, indigestible, unabsorbed material which increases the bulk of the intestinal contents, thereby producing reflex peristalsis and defecation. Psyllium is an excellent source of dietary fiber, the unabsorbed portion of ingested carbohydrate in our diet.

Apple fiber is a high quality source of both soluble and insoluble dietary fiber. It is high in pectin and therefore has excellent binding properties. Apple fiber is manufactured by removing the juice from the apple by a natural pressing process. The solids are then dried and ground into uniform particle sizes. Apple fiber is a less expensive source of fiber than is psyllium. Appropriate apple fiber, for use in the present composition, may be obtained from Tastee Apple in Newcomertown, Ohio.

Fructose is a monosaccharide and is the sweetest of all naturally occurring sugars. Fructose, usable in the product of the present invention is obtainable under the trademark "Crystar" sold by A. E. Staley Mgf. Co. in Decatur, Ill. Fructose has, in addition to its intense sweetness, flavor enhancing capabilities and a clean light mouthfeel. Additionally, it has been found that oral ingestion of fructose containing solutions can reduce appetite.

Gum arabic is produced by trees of the genus Acacia. Gum arabic is almost completely soluble in water and is used as a stabilizer in food. Gum arabic's main function in food is to impart desirable qualities through its influence over the viscosity, body and texture of foods and in the product of the present invention it is also used to enhance the mouthfeel of the product, and to add additional fiber content to the product.

Any appropriate, natural apple flavor may be used in the product of the present invention, but preferably a spray dried flavor is used. Apple flavor has been found to be a particular acceptable flavor to most people.

The mouthfeel of a laxative such as the laxative of the present invention is important. Psyllium containing products tend to be gritty and as such unpalatable. The product of the present invention has a superior mouthfeel which is achieved by controlling the particle size of the psyllium, apple fiber, and fructose components. It is important that the particles of all of the components in the product be smaller than a predetermined size. A preferred size is that of No. 50 U.S. Standard Screen. However, powders with particle sizes as great as a 40 mesh may be used to form an acceptable product. In one embodiment, the specification called for 98% of the particles to pass through a No. 50 mesh. The mouthfeel is also enhanced by the gum arabic.

A preferred weight percentage and an acceptable weight percentage range for the product of the present invention are set forth as follows:

TABLE I

| Ingredient | Preferred Weight by Percent | Weight Percentage Range |
|---|---|---|
| Psyllium Husk | 48% | 40-58% |
| Apple Fiber | 32.5% | 23-40% |
| Fructose | 17% | 12-40% |
| Apple Flavor | 2% | 1-4.5% |
| Gum Arabic | 0.5% | 0.3-2% |

The product of the present invention is a brownish gray powder which is intended to be mixed with water prior to ingestion. The recommended dosage of powder is a 7 gram dosage which contains approximately 9.1 calories per dose; between 44-49% carbohydrates by weight, as measured by the ASTA method; about 7% pectin by weight, as measured by the AOAC method, a moisture content of not more than 8% by weight as measured by the USP method, and a swell volume of approximately 55-60 ml per gram as measured by the USP method.

All of the ingredients of the present invention are natural. The use of fructose permits natural sweetening without excess calories and adds to the feeling of satiety imparted by the bulking effect of the psyllium.

What is claimed:

1. In a natural fiber laxative containing psyllium husk, sweetener, gum arabic and flavorants, the improvement comprising:
   apple fiber,
   said apple fiber and said psyllium husk constituting together at least 75% by weight of said composition,
   said psyllium husk being between 40% to 58% by weight of said composition, and
   said apple fiber being between 23% and 40% by weight of said composition.

2. The natural fiber laxative of claim 1 wherein said psyllium husk is about 48% by weight of said composition.

3. The natural fiber laxative of claim 2 wherein said apple fiber is about 32% by weight of said composition.

4. The natural fiber laxative of claim 1 wherein said apple fiber is about 32% by weight of said composition.

* * * * *